United States Patent [19]
Bendicks et al.

[11] Patent Number: 5,498,866
[45] Date of Patent: Mar. 12, 1996

[54] OPTOELECTRONIC SENSOR FOR DETECTING MOISTURE ON A WINDSHIELD WITH MEANS TO COMPENSATE FOR A METALLIC LAYER IN THE WINDSHIELD

[75] Inventors: orbert Bendicks, Hemer; Ralf Bartling, Dortmund, both of Germany

[73] Assignee: Leopold Kostal GmbH & Co. KG, Ludenscheid, Germany

[21] Appl. No.: 194,254

[22] Filed: Feb. 10, 1994

[30] Foreign Application Priority Data

Dec. 7, 1993 [DE] Germany ............... 43 18 114.7

[51] Int. Cl.⁶ ........................................... H01J 5/16
[52] U.S. Cl. ............... 250/227.25; 318/483; 318/DIG. 2
[58] Field of Search ............. 250/227.25; 318/483, 318/444, DIG. 2; 340/602

[56] References Cited

U.S. PATENT DOCUMENTS

| | | | |
|---|---|---|---|
| 4,481,450 | 11/1984 | Watanabe et al. | 318/444 |
| 4,859,867 | 8/1989 | Larson et al. | 307/10.1 |
| 4,960,996 | 10/1990 | Hochstein | 250/349 |
| 4,973,511 | 11/1990 | Farmer et al. | 428/216 |
| 5,323,637 | 6/1994 | Bendicks et al. | 73/29.01 |

Primary Examiner—David R. Hudspeth
Assistant Examiner—Steven L. Nichols
Attorney, Agent, or Firm—Brooks & Kushman

[57] ABSTRACT

A sensor device for detecting the degree of wetting of a multi-layer transparent pane, made in particular of glass, by an, in particular, drop-shaped precipitation. The sensor device is provided with a beam guide element which comprises two beam windows and cooperates with a beam transmitter and a beam receiver. In order to prevent spurious beams caused by an extremely thin intermediate layer located in the pane from having a noticeable influence on the signal used to control the windscreen wiper system, the beam guide element comprises a further beam exit window in the central region of its rear surface facing away from the pane. The region is located between the two beam windows. The further beam exit window is allocated to the measuring path and cooperates with an additional beam detector. Only those irrelevant beams reflected at the extremely thin metallic intermediate layer located in the pane exit therefrom. The signal resulting from the existing irrelevant beams which is detected by the additional beam detector is used to correct the signal supplied by the actual beam detector. Alternatively; signal correction can be achieved by an electrical circuit.

13 Claims, 6 Drawing Sheets

OPTOELECTRONIC SENSOR FOR DETECTING MOISTURE ON A WINDSHIELD WITH MEANS TO COMPENSATE FOR A METALLIC LAYER IN THE WINDSHIELD

TECHNICAL FIELD

This invention relates to a sensor device designed for detecting the degree of wetting of a transparent windscreen by a mainly drop-shaped precipitation.

BACKGROUND OF THE INVENTION

The particular purpose of optoelectronic sensor devices is to detect the quantity and/or quality in a representative form of the moisture precipitating per unit of time on the front or rear windscreen of a motor vehicle and in dependence thereupon, to influence automatically a windscreen wiping system allocated to the screen.

Devices for controlling a motor-driven windscreen wiping device have become known from DE 32 43 373 A1, DE 33 14 770 C2, DE 40 06 174 C1, DE 40 06 420 A1, DE 40 17 063 A1 and DE 40 19 066 A1, wherein by way of a beam guide element attached to the inner surface of a transparent windscreen, beams emitted from an associated beam transmitter are coupled into the transparent windscreen and after at least one reflection at the outer surface of the windscreen are decoupled again by way of the beam guide element and are directed to an associated beam receiver.

Some multi-layer windscreens installed nowadays in motor vehicles have an integrated intermediate metallic layer which is extremely thin and thus hardly impairs the transparency of the windscreen. This said intermediate layer is provided on the one hand to provide possible electrical heating of the windscreen and on the other hand to provide thermal insulation against infra-red rays which effect the motor vehicle from the outer side. This type of windscreen leads to the problem that the beams emitted by the beam transmitter are likewise reflected to a considerable extent at this intermediate layer and they are thus not available for the measuring process. Moreover, these beams stray as spurious beams in the beam guide element and they can thus have a negative influence on the signal supplied by the beam receiver. It has also been established that the spurious beams change in dependence upon the wavelengths of the beams emitted by the beam transmitter, these wave-lengths varying with the different temperatures.

SUMMARY OF THE INVENTION

In order to increase the size of the measuring area to be scanned with respect to achieving a representative result, it is possible for several measuring paths to be achieved in adjacent portions of the beam guide element which are preferably combined to form one block unit. This is attached in various ways for example by means of adhesive to the transparent windscreen.

The aim of the present invention is to develop further a sensor device in such a way that the spurious beams caused by an extremely thin intermediate layer located in the windscreen can have at least no noticeable influence on the signal used to control the windscreen wiper system.

This aim is achieved according to the invention by providing an optoelectronic sensor device wherein a front surface on a beam guide element is connected to the inner surface of a windshield beneath the wiping area covered by a motor-driven wiper device. The beam guide element has at least one measuring distance with a beam entry window and a beam exit window which is spatially separate-therefrom and is aligned at an angle of approximately 90° thereto. A beam transmitter is allocated to the beam entry window. A beam receiver is allocated to the beam exit window. Beams emitted by the beam transmitter are reflected in dependence upon the precipitation present on the windshield and directed to the beam receiver which in each case provides a signal dependent upon the associated quantity of precipitation.

Compensating means are provided in order to correct the signal supplied by the beam detector and resulting from the quantity of mixed beams. Such correction is dependent upon the quantity of spurious beams reflected at an extremely thin and thus partially transparent metallic intermediate layer located within the windshield.

The advantage with such a development is that by measuring the pure portion of spurious or irrelevant beams and by measuring the portion of spurious/useful beams it is possible to produce a relationship between these variables. This relationship, if necessary, can be used to balance the variations occurring during the manufacture of the windscreen, such as of the thickness of the windscreen or the characteristics of the layer.

Further particularly advantageous developments of the device according to the invention are indicated in dependent claims and are described in greater detail with reference to two embodiments, which are illustrated in the drawings.

Also disclosed is a method for improving the sensitivity of a rain-sensing system based on infra-red light in connection with a heated windscreen, windshield, or electriclear glass.

Figure 1:
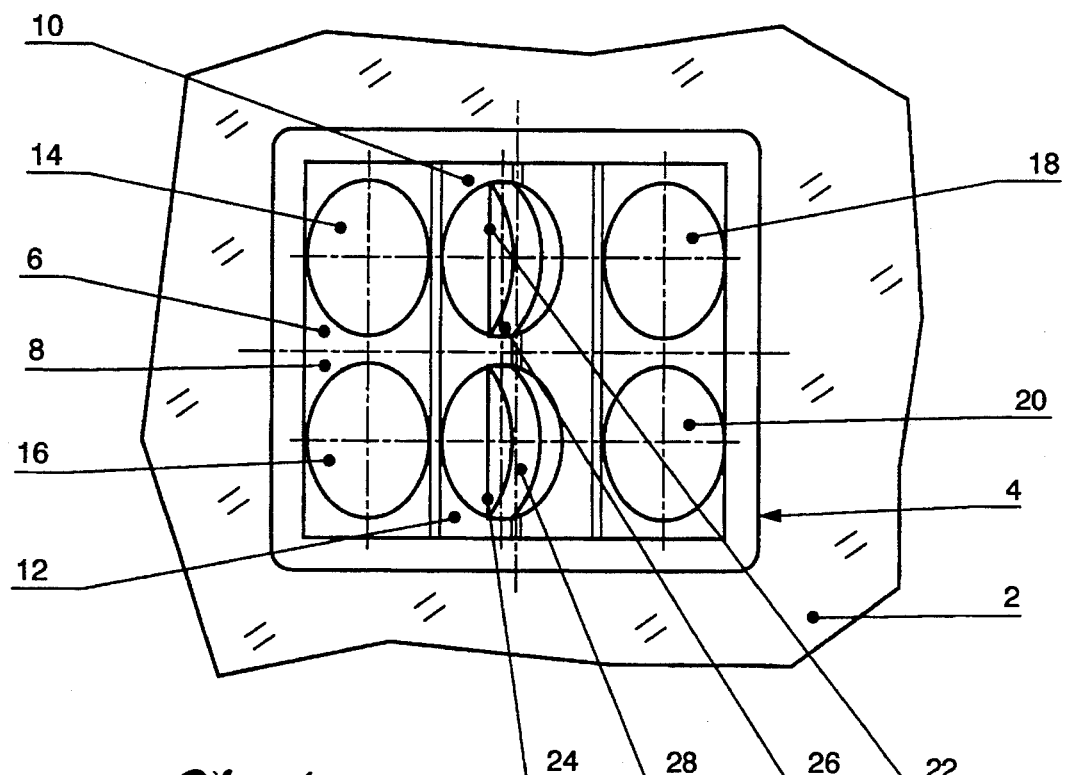
FIG. 1, a view of the beam guide element from a sensor device attached to a windscreen.

Corresponding components in the figures have been provided with the same designations.

BEST MODE FOR CARRYING OUT THE INVENTION

As the drawings show, a sensor device for detecting the degree of wetting of a preferably glass pane 1 by, in particular, drop-shaped precipitation comprises two beam transmitters 3', 3" (one only indicated for the sake of simplicity) and two beam receivers 4', 4" (likewise one only indicated for the sake of simplicity), a beam guide element 2 formed from two parallel lying portions 2a, 2b, which is attached by means of optical adhesive to the inner surface 1' of the pane 1 not exposed to the precipitation.

The pane 1 is in particular the windscreen of a motor vehicle on which the sensor device, disposed in a housing (also not shown for the sake of simplicity), is provided at an exposed point, i.e. a point of the inner surface 1' which does not impair vision but is predetermined for detecting the precipitation. The pane 1 is, as is usual nowadays for safety reasons, a composite pane comprising two layers 1a and 1b as well as a film 1c located between the two. In order with a pane of this type to provide insulation against infra-red rays which strike the outside of the pane and to provide heating for the pane, an extremely thin metallic intermediate layer 1d is installed in the pane 1 in the region of the film 1c.

The beam guide element 2 consisting of the portions 2a, 2b comprises two support parts 2a', 2a" which are mechanically interconnected and optically separated from each other. In each case a beam lens 2b*, 2b** and 2c*, 2c** is disposed with its planar base surface at the support parts 2a', 2a" lying opposite in each case the beam windows 2b', 2b" and 2c', 2c". The identically sized beam windows 2b', 2b" and 2c', 2c" are disposed at the support parts 2a', 2a" in such a way that the center lines of the beam lenses 2b*, 2b** and 2c*, 2c** are offset with respect to each other by an angle of approximately 90°. The beam lenses may be either fixed by their planar bases on the beam windows for example with the aid of a respective centering dowel and optical adhesive or may be integrally formed directly on the support parts.

An additional beam exit window 2d', 2d" is provided in the respective central region of the two support parts 2a', 2a", i.e. between the actual beam windows 2b' and 2c' and 2b" and 2c" and each beam exit window is allocated an additional beam detector 5' (5"), 6. The beam exit windows 2d', 2d" are disposed parallel to and directly adjacent to the actual beam exit windows 2c', 2c". These windows are, however, owing to spatial restrictions located in different planes.

Figure 2:
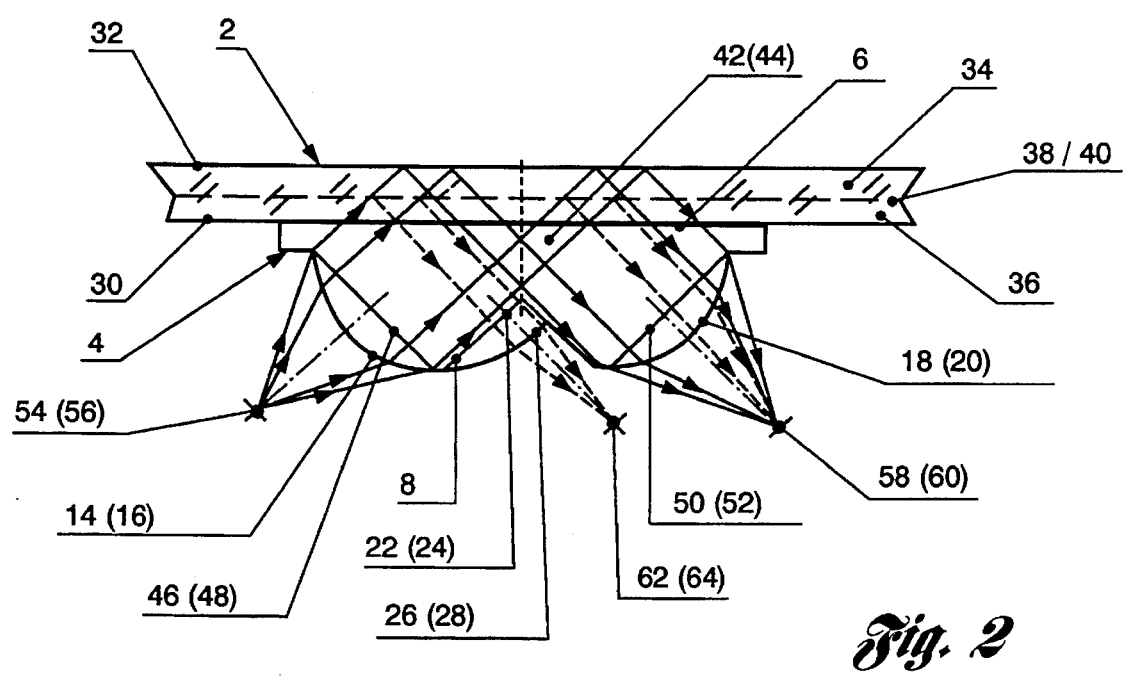
FIG. 2, a side view of the beam guide element as in FIG. 1.

As shown in FIGS. 1 and 2, the two additional beam exit windows 2d', 2d" correspond in width to the width extension of the beams in the respective measuring paths. The height of the said beam exit windows is dependent upon the spacing of the metallic intermediate layer 1d with respect to the surface 1' of the pane 1. The beam exit windows are provided in each case with an additional beam lens 2d*, 2d** formed as a correspondingly designed portion of a non-spherical lens configuration. An additional beam detector 5', 5" is then allocated in each case to the additional beam exit windows 2d', 2d" and the additional beam lenses 2d*, 2d**. As is evident from the schematic graph of the beam paths in FIG. 2, only those spurious beams reflected at the metallic intermediate layer 1d are received by the two additional beam detectors 5', 5", whereas the two actual beam receivers 4', 4" are influenced by a mixture of beams which comprise useful beams reflected by the outer surface 1" of the pane 1 and spurious beams reflected at the metallic intermediate layer 1d.

The arrangement of the additional beam windows 2d', 2d", the additional beam detectors 5', 5", and the allocation with respect to the actual beam exit windows 2c', 2c" and the actual beam receivers 4', 4" produces a quasi clear geometrical relationship between the amount of spurious beams emerging at the additional beam exit windows 2d', 2d" respectively. Consequently, it is possible with the aid of an analogue or digital compensating stage (not illustrated for the sake of simplicity) downstream of the actual beam receivers 4', 4" and the additional beam detectors 5', 5" to correct correspondingly the signal which is emitted by the actual beam receivers 4', 4" respectively, which signal is dependent upon the transmission characteristics and varies in wave length with the temperature.

Figure 3:
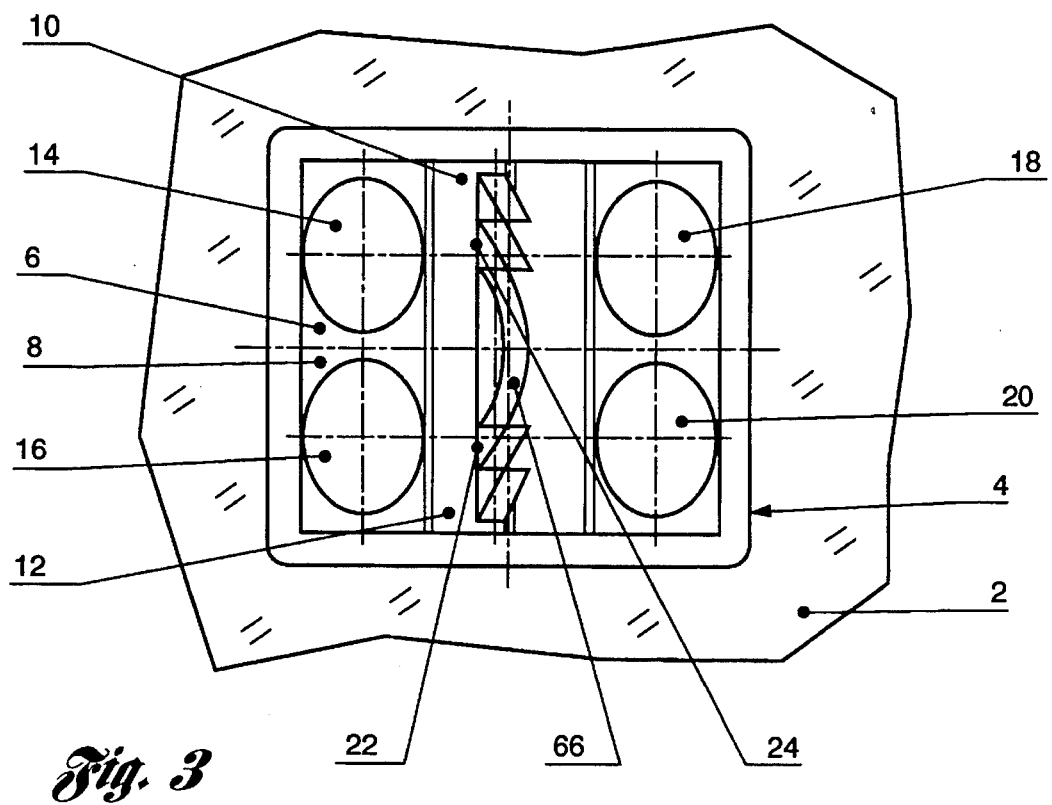
FIG. 3, a view of a different beam guide element from a sensor device attached to a windscreen.
Figure 4:
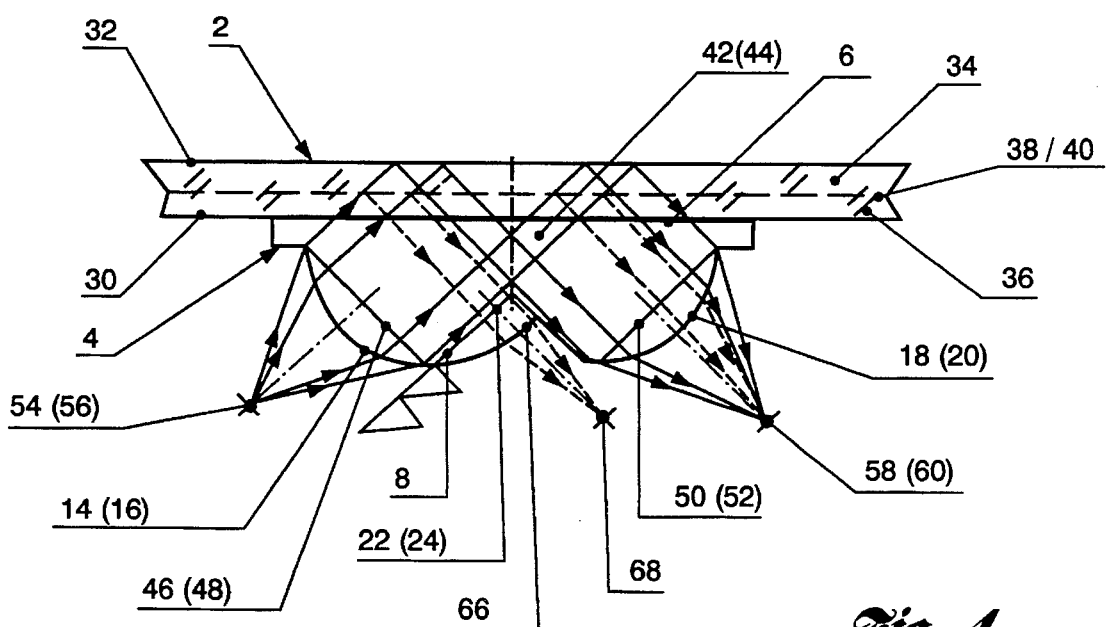
FIG. 4, a side view of the beam guide element as in FIG. 3.

In accordance with the embodiment shown in FIGS. 3 and 4, a simplified construction is facilitated by the use of a sensor device comprising two measuring paths are produced by a common fresnel-lens-type beam lens 2e" which is allocated to the two additional beam windows 2d', 2d". The beam lens cooperates with an additional beam detector 6. In this type of configuration, the two measuring distances are interrogated successively and the output signals of the two actual beam receivers 4', 4" are influenced in dependence thereupon.

The present invention also discloses a method for improving the sensitivity of a rain-sensing system based on infrared light in connection with a heated windscreen, windshield, or electriclear glass.

1. Description Of The Measuring Technique

The disclosed rain-sensing system functions as follows. The rain sensor is attached at the windshield inside the motor vehicle in the wiping region of the windscreen wiper. An infra-red ray is transmitted by an LED and directed through the windscreen. The light beam is totally reflected at the boundary layer windscreen-air owing to the acute angle. The light so reflected is then received again by a photodiode. Should a wetting of the screen occur, then a portion of the light beam is deflected to the outside and no longer reflected at the boundary layer. Consequently, less light arrives at the photodiode and a wiping cycle is eventually triggered. The transmitting diodes work with a predetermined frequency which is filtered out again at the receiving side with a phase-selective rectifier. This feature renders possible a rain-sensing system of this type which to a large extent is independent of any influences from the surrounding light.

2. Problems With A Heated Windscreen

It has been established when installing this type of rain-sensing system on a heated windscreen that the sensitivity severely reduces in comparison to a normal windscreen.

Figure 5:
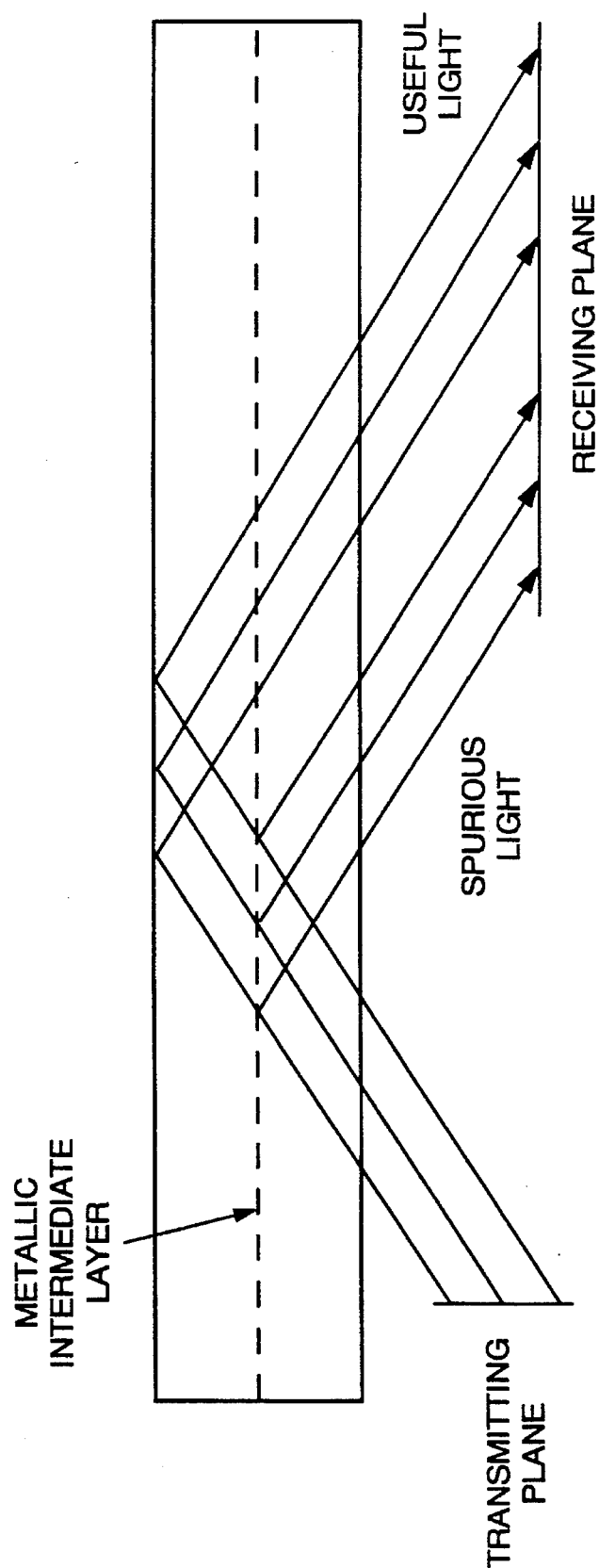
FIG. 5 illustrates a heated windshield with a metallic layer, including a transmitting plane, spurious light, useful light, and a receiving plane.

The cause of this effect is the metallic layer in the center of the composite glass (see FIG. 5). The boundary layer glass-air is not the first place where the light beam of the rain sensor is reflected, as the light beam has already been reflected at the metallic inner layer in the composite glass. Consequently, a relatively high constant portion of noise signal which does not change when wetting occurs, is measured in the output signal of the rain sensor.

Accurate measurements have shown that approximately 70% of the infra-red light is already reflected inside the screen.

3. Description Of The Active Compensating Circuitry

Figure 6:
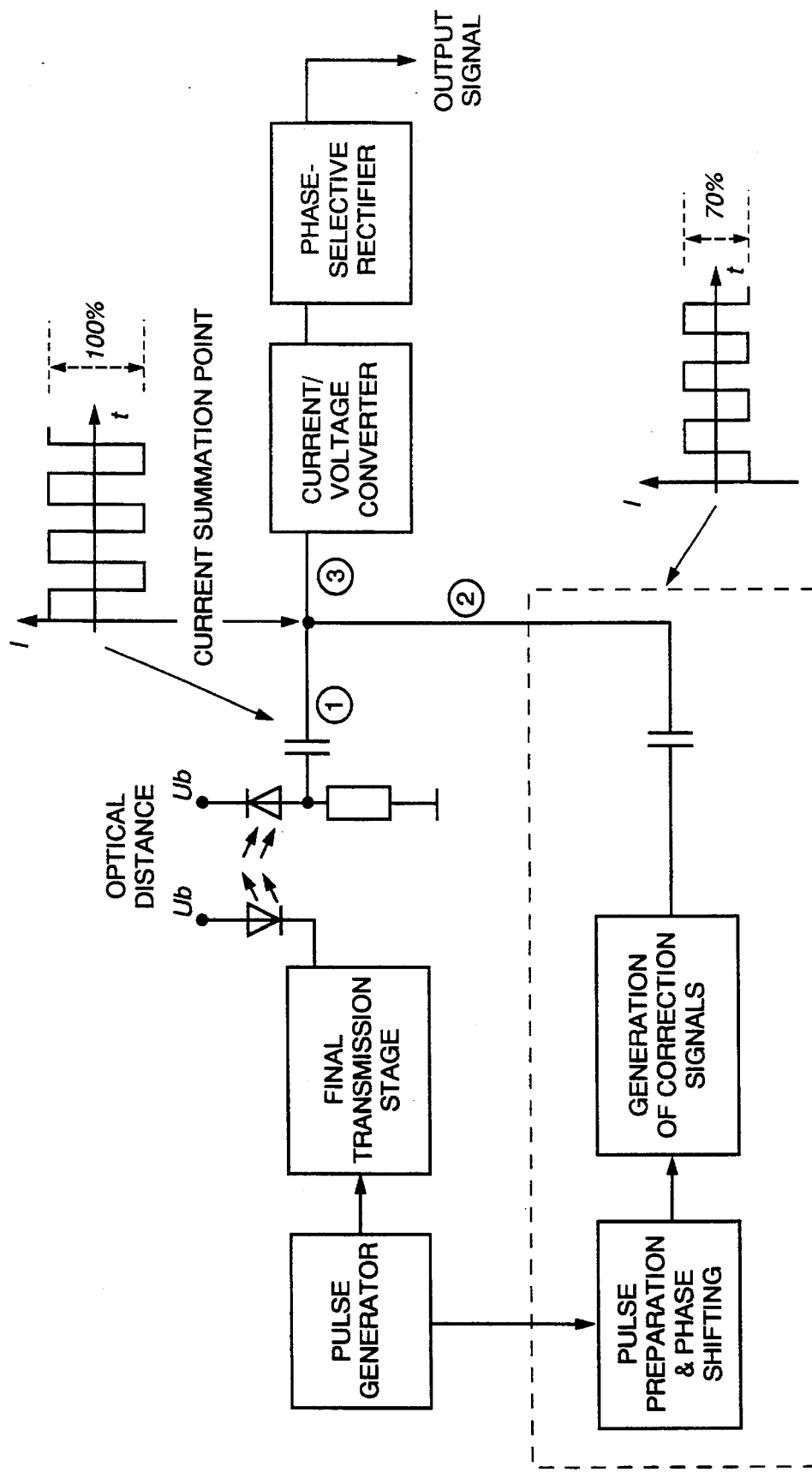
FIG. 6 is a block diagram of a rain-sensing system with active compensation.
Figure 7:
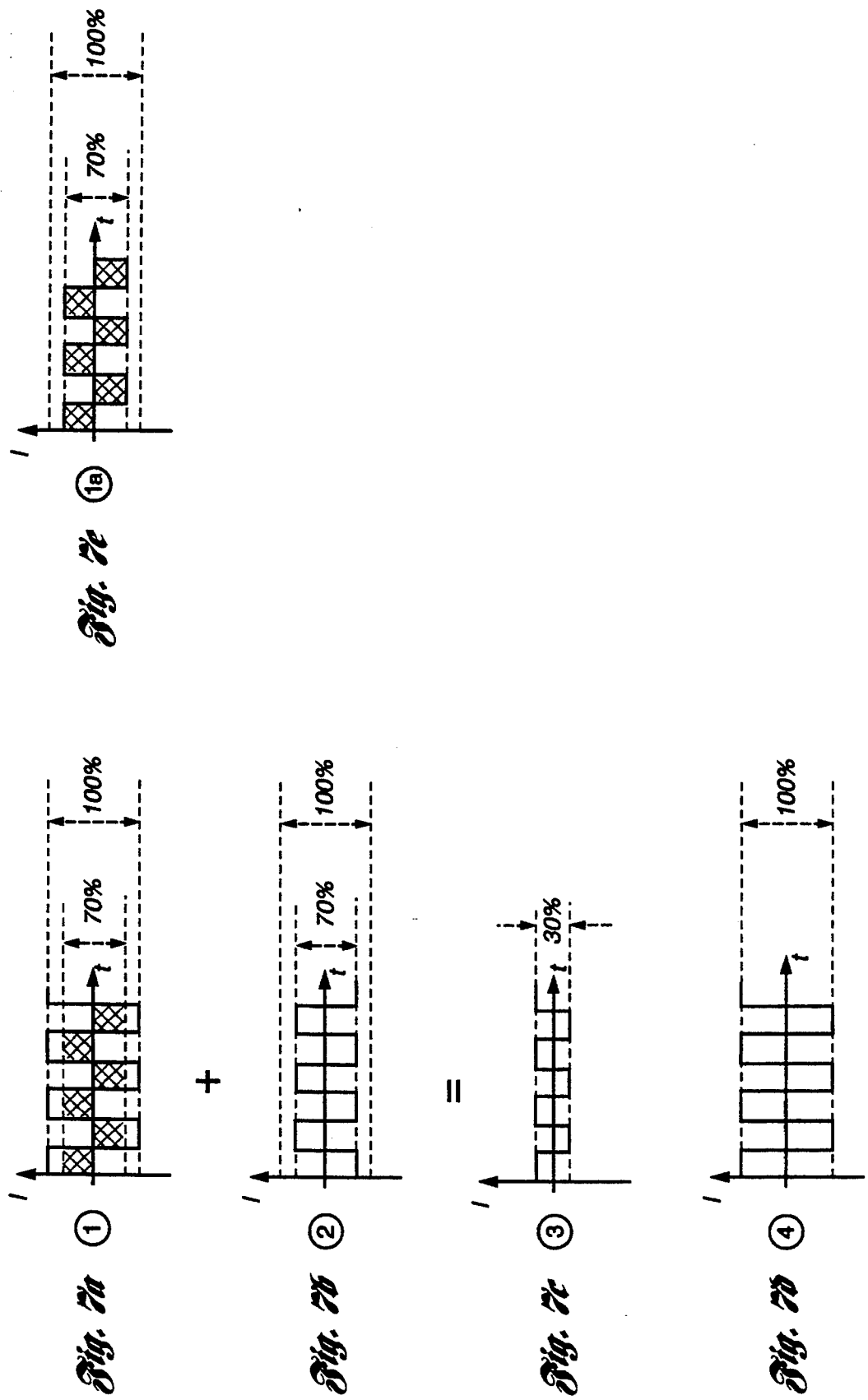
FIG. 7 is a time graph of the currents such as they occur when using active compensation.
Figure 8:
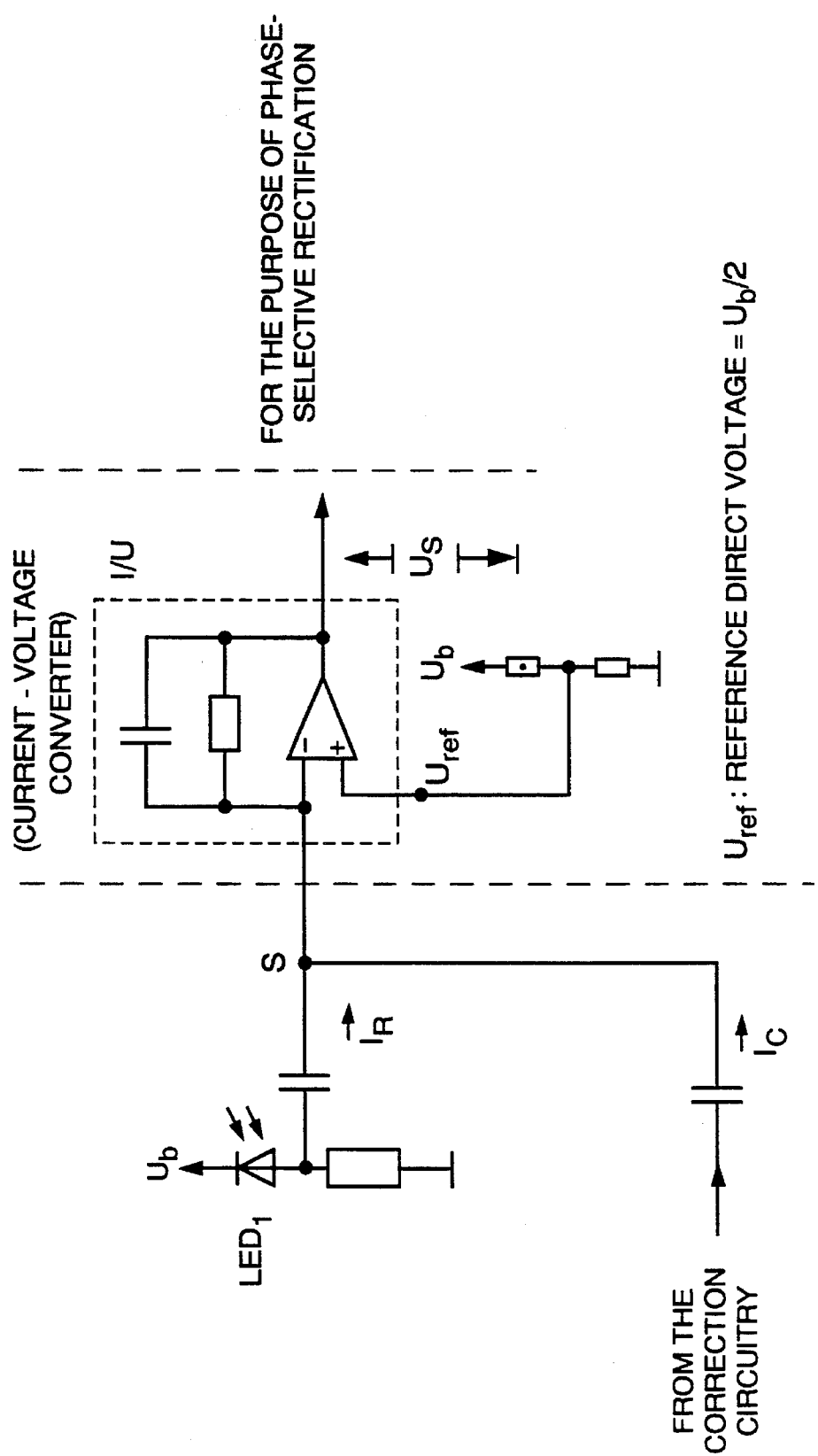
FIG. 8 depicts representative circuitry suitable in the present invention.

Turning now to FIGS. 6–8, FIG. 6 illustrates the block diagram of a rain-sensing system with active compensation. In that figure, there is depicted a current/voltage converter 3 for the purpose of phase-selective rectification. The time graph of the currents, such as occur when using an active compensation, is illustrated in FIG. 7.

Item 1 (FIG. 7)

This illustrates the receiving current. It consists of a constant noise portion of approximately 70% which is caused by the direct reflection at the reflective layer internal to windscreen and a variable portion which can lie from 0% to 30%. Full modulation occurs in FIG. 5, whereas there is no modulation in Diagram 1a (FIG. 7). Using a windscreen without a reflective internal layer, where the signal is completely decoupled at the outside surface, it is not possible to measure any current at all. However, owing to the direct reflection at the internal reflective layer of the windscreen, the current does not fall below 70%.

Item 2 (FIG. 7)

This illustrates the compensating signal. This signal is generated which is phase-shifted by 180° relative to the receiving currents and has an amplitude which corresponds exactly to the amplitude of the constant portion in the receiving current.

In Item 1 (FIG. 7), the receiving current and the compensating current are superimposed at the current summation point S (shown in FIG. 8). This represents mathematically an addition, with the constant portion being compensated exactly in the receiving current. It is important to couple in a current actively (which is related to the transmitted current) at the current summation point, since in this way only the useful portion is maintained in the receiving current. Should the voltage be simply divided at this point, then the small useful voltage portion would also be subdivided.

Item 3 (FIG. 7)

This illustrates the summation of the receiving current and the compensating current. The amplitude of the signal amounts only to approximately 30% of the original receiving current. However, this current can vary from zero to full amplitude in dependence upon an external wetting.

Item 4 (FIG. 7)

The original signal amplitude is achieved again by increasing the amplifying factor of the current/voltage converter. It must, however, be fully understood that by virtue of this circuitry with only approximately 30% of the available light, a signal amplitude of almost 100% is produced "artificially." The result of this feature is a deterioration in the signal-to-noise ratio. The rain-sensing system would usually provide a sufficient signal-to-noise ratio when using a compensating circuitry of this type.

A method for improving the sensitivity of a rain-sensing system based on infra-red light in connection with a heated windscreen (heated windshield or electriclear glass) is depicted in FIG. 8, which illustrates representative circuitry suitable for implementing the present invention.

FIG. 8 depicts two current components, $I_R$ and $I_C$, which are summed and introduced at the input portion (point "S") of the current to voltage convertor circuit (indicated as I/U). $I_R$ represents an oscillating current which is a combination of useful and noise signals received by LED 1. $I_C$ represents an oscillating compensation current generated by circuitry which adjusts the current magnitude relative to the expected signal as presented earlier. $I_R$ and $I_C$ are phase shifted 180° relative to each other. $U_{REF}$, voltage proportional to the source for the received signal current, $I_R$, is introduced at the second input to the current to voltage convertor circuit I/U.

The output from I/U, $V_S$, is an oscillating voltage which represents a noise reduced/eliminated signal.

What is claimed is:

1. An optoelectronic sensor device for detecting the degree of wetting of a multi-layer transparent pane by drop-shaped precipitation, the sensor device comprising:

a beam guide element having a front surface connected to an inner surface of the pane not exposed to the precipitation in a region of a wiping area covered by a motor driven windscreen wiper device, the beam guide element having at least one measuring path with a beam entry window and first and second beam exit windows;

a beam transmitter associated with the beam entry window;

a first beam detector associated with the first beam exit window in such a manner that beams emitted by the beam transmitter are reflected in dependence upon the precipitation present on the pane and directed to the first beam detector, which provides a first signal dependent upon the associated quantity of precipitation;

a second beam detector associated with the second beam exit window in such a manner that only spurious beams reflected at a partially transparent metallic intermediate layer located in the pane are detected by the second beam detector, which provides a second signal representative of a quantity of the spurious beams; and compensating means for correcting the first signal supplied by the first beam detector and representative of a quantity of mixed beams including useful beams and spurious beams, the correction being dependent upon the second signal supplied by the second beam detector.

2. The sensor device of claim 1, wherein the second beam exit window is disposed in a plane which lies parallel to the plane of the first beam exit window.

3. The sensor device of claim 2, wherein the second beam exit window is directly adjacent to the first beam exit window.

4. The sensor device of claim 1, wherein all beam windows have an associated beam lens.

5. The sensor device of claim 1, wherein the second beam exit window has a width corresponding to the width extension of the beams in the measuring path, and a height dependent upon the spacing of the metallic intermediate layer relative to the inner surface of the pane, a beam lens being allocated thereto and designed as a corresponding portion of an aspherical lens topography.

6. The sensor device of claim 5, further comprising two measuring paths extending in parallel adjacent to each other, a correspondingly designed portion of a fresnel-lens-type lens configuration being provided for both measuring paths together.

7. The sensor device of claim 1, wherein the compensating means comprises a plurality of electrical components which produce an electrical correction signal, the correction signal being phase-shifted and supplied to a current summation point located electrically behind the first beam detector.

8. The sensor device of claim 7, wherein the electrical components include a pulse-preparation stage and a phase-shifting stage as well as a correcting stage disposed electrically downstream thereof, the phase-shifting stage lying at the current summation point with its output over a capacitor provided for the purpose of suppressing a direct current portion, the pulse-preparation stage and phase-shifting stage being connected with the phase shifting stage input at the output of the pulse stage; the input of the pulse stage being connected to the output of a final stage associated with the first beam detector.

9. The sensor device of claim 8, wherein the output of the first beam detector is placed over a resistance to earth; a capacitor, provided for suppressing the direct current portion, being connected at one side to the electrical connection between the first beam detector and the associated resistance, said capacitor being connected at the other side to the current summation point which is associated with a current-voltage conversion stage as part of evaluation circuitry; and a phase-selective rectification stage being connected to the current-voltage conversion stage.

10. An optoelectronic sensor device for detecting the degree of wetting a multi-layer transparent pane by drop-shaped precipitation, the sensor device comprising:

a beam guide element having a front surface connected to an inner surface of the pane not exposed to the precipitation in a region of a wiping area covered by a motor driven windscreen wiper device, the beam guide element having at least one measuring path with a beam entry window and a first beam exit window spatially separate therefrom and aligned at an angle of approximately 90° thereto;

a beam transmitter associated with the beam entry window;

a first beam detector associated with the first beam exit window in such a manner that beams emitted by the beam transmitter are reflected in dependence upon the precipitation present on the pane and directed to the first beam detector, which in each case provides a first signal dependent upon the associated quantity of precipitation; and compensating means for correcting the first signal supplied by the first beam detector and resulting from a quantity of mixed beams, the correction being dependent upon a quantity of spurious beams reflected at a partially transparent metallic intermediate layer located in the pane;

the beam guide element further comprising a second beam exit window, which is allocated to the measuring path and cooperates with a second beam detector, the second beam exit window being situated in a central region of a rear surface of the beam guide element facing away from the pane, said region being located between the two beam windows so that only those spurious beams reflected at the metallic intermediate layer in the pane exit from the second beam exit window and are detected by the second beam detector, which provides a second signal resulting from a quantity of the exiting spurious beams for use in correcting the first signal supplied by the first beam detector, the first signal resulting from a quantity of mixed beams composed of beams exiting the first beam exit window, and beams from a useful beam portion and a spurious beam portion, said quantity of mixed beams having a quasi clear geometrical relationship to the quantity exiting from the second beam exit window;

wherein the second beam exit window has a width corresponding to the width extension of the beams in the measuring path, and a height dependent upon the spacing of the metallic intermediate layer relative to the inner surface the pane, a beam lens being allocated thereto and designed as a corresponding portion of an aspherical lens topography.

11. The sensor device of claim 10 further comprising two measuring paths extending in parallel adjacent to each other, a correspondingly designed portion of a fresnel-lens-type lens configuration being provided for both measuring paths together.

12. An optoelectronic sensor device for detecting the degree of wetting a multi-layer transparent pane by drop-shaped precipitation, the sensor device comprising:

a beam guide element having a front surface connected to an inner surface of the pane not exposed to the precipitation in a region of a wiping area covered by a motor driven windscreen wiper device, the beam guide element having at least one measuring path with a beam entry window and a beam exit window spatially separate therefrom and aligned at an angle of approximately 90° thereto;

a beam transmitter associated with the beam entry window;

a beam detector associated with the beam exit window in such a manner that beams emitted by the beam transmitter are reflected in dependence upon the precipitation present on the pane and directed to the beam detector, which in each case provides a signal dependent upon the associated quantity of precipitation; and compensating means for correcting the signal supplied by the beam detector and resulting from a quantity of mixed beams, the correction being dependent upon a quantity of spurious beams reflected at a partially transparent metallic intermediate layer located in the pane, the compensating means comprising a plurality of electrical components which produce an electrical correction signal, the correction signal, in contrast to the signal supplied by the beam detector, being phase-shifted and supplied to a current summation point located electrically behind the beam detector, the electrical components including a pulse-preparation stage and a phase-shifting stage as well as a correcting stage disposed electrically downstream thereof, the phase-shifting stage lying at the current summation point with its output over a capacitor provided for the purpose of suppressing a direct current portion, the pulse-preparation stage and phase-shifting stage being connected with the phase shifting stage input at the output of the pulse stage; the input of the pulse stage being connected to the output of a final stage associated with the beam detector.

13. The sensor device of claim 12 wherein the output of the beam detector is placed over a resistance to earth; a capacitor, provided for suppressing the direct current portion, being connected at one side to the electrical connection between the beam detector and the associated resistance, said capacitor being connected at the other side to the current summation point which is associated with a current-voltage conversion stage as part of evaluation circuitry; and a phase-selective rectification stage being connected to the current-voltage conversion stage.

* * * * *